US00PP28856P3

(12) United States Plant Patent
Vitten et al.

(10) Patent No.: US PP28,856 P3
(45) Date of Patent: Jan. 9, 2018

(54) RASPBERRY PLANT NAMED 'DRISRASPNINE'

(50) Latin Name: ***Rubus idaeus* L.**
Varietal Denomination: DrisRaspNine

(71) Applicant: Driscoll's, Inc., Watsonville, CA (US)

(72) Inventors: Matthias D. Vitten, Aptos, CA (US); Brian K. Hamilton, Richmond, TX (US); Moises D. Gonzalez, Fillmore, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 14/999,293

(22) Filed: Apr. 21, 2016

(65) Prior Publication Data

US 2017/0311501 P1 Oct. 26, 2017

(51) Int. Cl.
*A01H 5/08* (2006.01)

(52) U.S. Cl.
USPC ..... Plt./204

(58) Field of Classification Search
USPC ..... Plt./204
CPC ..... A01H 5/0887
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| 2016/0219774 | P1 | 7/2016 | Hamilton et al. |

OTHER PUBLICATIONS

Cousineau et al. "Use of Isoenzyme Analysis to Characterize Raspberry Cultivars and Detect Cultivar Mislabeling", HortScience, vol. 27, No. 9, 1992, pp. 1023-1025.
Hamilton, Brian K., U.S. Appl. No. 14/999,878, filed Jul. 13, 2016, titled "Raspberry Plant Variety Named 'Drisraspten'".
Williams et al. "Dna Polymorphisms Amplified by Arbitrary Primers are Useful As Genetic Markers", Nucleic Acids Research, vol. 18, No. 22, 1990, pp. 6531-6535.

*Primary Examiner* — Kent L Bell
(74) *Attorney, Agent, or Firm* — Morrison & Foerster LLP

(57) ABSTRACT

A new and distinct variety of raspberry plant named 'DrisRaspNine' particularly distinguished by having a self-fruitful plant that bears medium-sized, strongly red berries, is disclosed.

2 Drawing Sheets

Genus and species: *Rubus idaeus* L.
Variety denomination: 'DrisRaspNine'.

BACKGROUND OF THE NEW PLANT

The present invention relates to a new and distinct raspberry variety designated 'DrisRaspNine' and botanically known as *Rubus idaeus* L. This new raspberry variety was discovered in Ventura County, Calif. in February 2011 and originated from a cross between the proprietary female parent raspberry plant 'RB629.4' (unpatented) and the proprietary male parent raspberry plant 'RB629.5' (unpatented). The original seedling of the new variety was first asexually propagated at a nursery in Santa Cruz County, Calif. in 2011. 'DrisRaspNine' was subsequently asexually propagated and underwent further testing at a nursery in Ventura County, Calif. for five years. The present invention has been found to be stable and reproduce true to type through successive asexual propagations via tissue culture and root cuttings.

SUMMARY OF THE INVENTION

The following are the most outstanding and distinguishing characteristics of this new variety when grown under normal horticultural practices in Ventura, Calif.:

1. Self-fruitful plant; and
2. Medium-sized, strongly red berries.

DESCRIPTION OF THE PHOTOGRAPHS

This new raspberry plant is illustrated by the accompanying photographs which show fruit, flowers and leaves of the new plant. The colors shown are as true as can be reasonably obtained by conventional photographic procedures. The photographs are of plants that are six months old.

DESCRIPTION OF THE NEW VARIETY

Figure 1:
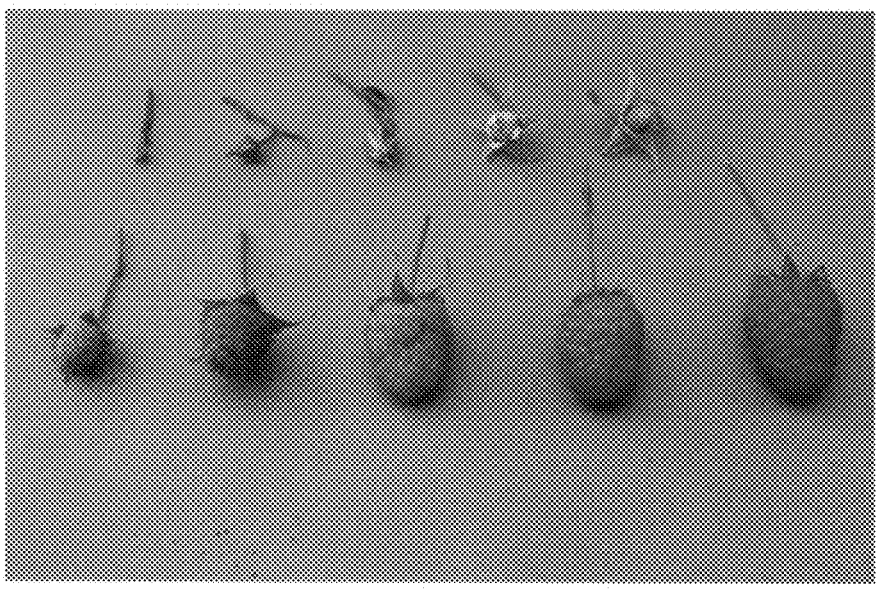
FIG. 1 shows close-up views of typical flowers and fruit at various stages of development.
Figure 2:
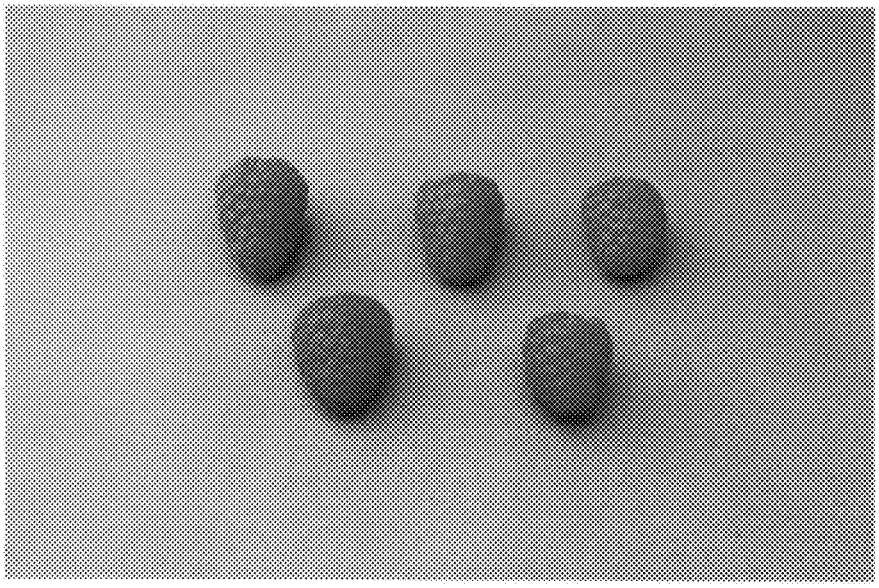
FIG. 2 shows a close-up view of fruit.
Figure 3:
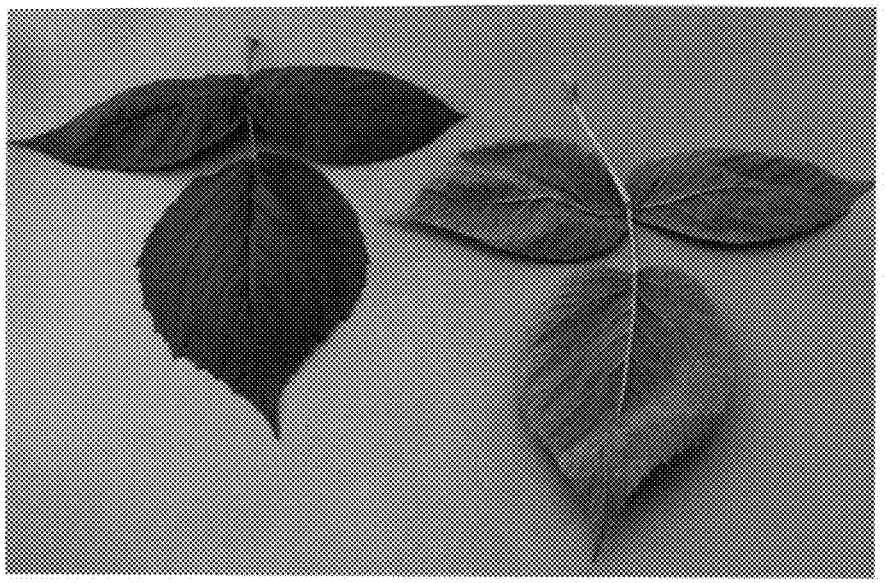
FIG. 3 shows both the upper surface and the lower surface of the plant leaves.

The following detailed descriptions set forth the distinctive characteristics of 'DrisRaspNine'. The data which define these characteristics is based on observations taken in Ventura County, Calif. from 2011 to 2015. This description is in accordance with UPOV terminology. Color designations, color descriptions, and other phenotypical descriptions may deviate from the stated values and descriptions depending upon variation in environmental, seasonal, climatic and cultural conditions. 'DrisRaspNine' has not been observed under all possible environmental conditions. The botanical description of 'DrisRaspNine' was taken from six-month-old plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family*.—Rosaceae.

*Botanical*.—*Rubus idaeus* L.

*Common name*.—Raspberry.

*Variety name*.—'DrisRaspNine'.

Parentage:

*Female parent*.—The proprietary raspberry plant 'RB629.4' (unpatented).

*Male parent*.—The proprietary raspberry plant 'RB629.5' (unpatented).

Plant:

*Propagation*.—Tissue culture and root cuttings.

*Size*.—Medium.

*Height*.—145.2 cm.

*Width*.—133.2 cm.

*Length/width ratio*.—1.1.

*Productivity*.—Productivity of plants that were one-year old (primocanes) ranged from 4.56 kg per meter of planting of 'DrisRaspNine' to 5.08 kg per meter of planting of 'DrisRaspNine' of fruit per season when grown in Oxnard, Calif.; and productivity of plants that were two-years old (floricanes) ranged from 5.39 kg per meter of planting of 'DrisRaspNine' to 6.62 kg per meter of planting of 'DrisRaspNine' of fruit per season when grown in Oxnard, Calif.

*Self-fruitfulness*.—Self-fruitful.

*New cane growth habit*.—Semi-erect.

Primocanes:

*Number of canes*.—31.

*Glaucosity (waxy bloom) on full grown shoot after picking*.—Medium.

*Cane length in autumn*.—Short.

*Cane length for current season's cane in autumn*.—148.7 cm.

*Cane diameter*.—9.1 mm.

*Length of internode*.—Medium.

*Internodal distance at central ⅓ of cane*.—7.5 cm.

*Length of vegetative bud*.—8.2 mm.

*Anthocyanin coloration of apex during rapid growth*.—RHS N34C.

*Intensity of anthocyanin coloration of apex during rapid growth*.—Weak.

*Time of cane emergence*.—March.

*Time of beginning of flowers*.—Early June.

*Time of beginning of fruit ripening in autumn*.—Late June to early July.

*Length of fruiting period in autumn*.—July to September.

*Percent of cane flowering as primocane*.—45%.

*Percent primocane yield of total yield*.—46%.

*Glaucosity (waxy bloom) on current years cane in autumn*.—Medium.

*Cane strength*.—Strong.

*Shape of cane cross section*.—Rounded.

*Pubescence on canes*.—Absent.

Floricanes:

*Dormant cane length in summer*.—39 inches after winter prune.

*Dormant cane diameter in summer*.—9.9 mm.

*Dormant cane color in summer*.—RHS 175A and 165B (Moderate red-brown and brown-orange); RHS 185C (Moderate purple-red) with bloom.

*Fruiting lateral attitude*.—Semi-erect.

*Fruiting lateral length*.—38.5 inches.

*Fruiting lateral diameter*.—7.4 mm.

*Time of vegetative bud burst*.—March.

*Time of beginning of flowers*.—April.

*Time of beginning of fruit ripening*.—May.

*Length of fruiting period*.—May to early July.

Prickles (spines):

*Density of spines on central third*.—3 spines/10 mm$^2$.

*Length of base of prickles*.—0.8 mm.

*Length (from base to tip)*.—2.10 mmLength at 1.0 m height at end of harvest season (from base to tip): 0.52 mm.

*Color (pigmentation)*.—RHS 199A (Moderate olive-brown).

*Attitude of tip*.—Downward.

*Texture*.—Short and rigid.

*Presence and distribution on petioles*.—Present and regularly distributed.

Leaves:

*Terminal leaflet*.—Length: Medium; 138.7 mm. Width: Medium; 89.4 mm. Length/width ratio: 1.6. Leaf color: Upper surface: RHS N137A (Moderate olive-green). Lower surface: RHS 148B (Moderate yellow-green). Profile in cross section: Convex. Relief between the veins: Medium. Overlapping of leaflets: Free. Glossiness: Medium. Shape: Ovate. Apex: Truncate. Base: Obtuse. Margin: Serrate. Arrangement: Simple.

*Lateral leaflets (basal pair)*.—Number of leaflets: Usually 3. Size: Length: 113.4 mm. Width: 67.5 mm. Length/width ratio: 1.7. Arrangement: Compound-opposite (2 leaves per node). Shape: Ovate. Apex: Truncate. Base: Obtuse. Margin: Doubly serrate. Lateral leaflet (length to stalklet, lower pair): Medium.

*Rachis length between terminal leaflet and adjacent lateral leaflets*.—38.8 mm.

*Rachis diameter*.—1.7 mm.

*Petiole*.—Size: Length: 61.1 mm. Diameter: 2.45 mm. Pigmentation: Upper surface: RHS 59B (Deep purple-red). Lower surface: RHS 59B (Deep purple-red).

*Stipules*.—Orientation: Reflexed. Number: 2. Length: 7.1 mm. Width: 0.3 mm. Color: Upper surface: RHS 144A. Lower surface: RHS N144D.

Flowers:

*Size*.—Medium.

*Diameter*.—29.4 mm.

*Color*.—RHS 155C (Green-white).

*Petal length*.—9.08 mm.

*Petal width*.—4.04 mm.

*Length/width ratio*.—2.2.

*Flowering period*.—Primocane: Begins in early June. Floricane: Begins in April.

*Pedicel*.—Number of spines: 4 spines/2 $mm^2$. Anthocyanin coloration: Absent. Length: Long; 52.9 mm. Diameter: 1.09 mm. Color: RHS 144B.

*Peduncle*.—Presence of anthocyanin coloration: Absent. Intensity of anthocyanin coloration: Weak. Length: 65.7 mm. Width: 1.3 mm. Color: RHS 144C.

Fruit:

*Length*.—Medium; 24.7 mm.

*Width*.—Medium; 22.8 mm.

*Ratio of length to width*.—1.1, longer than broad.

*Average number of drupelets per fruit*.—91.

*Weight* (*g/fruit*).—Primocane: 4.8. Floricane: 4.5.

*Soluble solids* (*% in Brix*).—10.2.

*Weight of seeds* (*g/seed*).—0.013.

*Size*.—Medium.

*Shape*.—Ovate (Broad conical).

*Length of single drupelet*.—3.2 mm.

*Width of single drupelet*.—4.0 mm.

*Color*.—Immature fruit: RHS 152C (Dark green-yellow). Maturing fruit: RHS 33B (Vivid red-orange). Mature fruit color: RHS 47B (Strong red).

*Glossiness*.—Medium.

*Firmness*.—Soft.

*Adherence to plug*.—Easy.

*Main bearing type*.—Both on previous year's cane in summer and on current year's cane in autumn. Time of ripening: Primocane: July to September. Floricane: May to early June. Harvest season: Primocane: Planted August 15, harvested December to February. Floricane: Harvested May to November, in California.

*Yield*.—Yield from plants that were one-year old (primocanes): ranged from 4.56 kg per meter of planting of 'DrisRaspNine' to 5.08 kg per meter of planting of 'DrisRaspNine' of fruit per season when grown in Oxnard, Calif.; and yield from plants that were two-years old (floricanes) ranged from 5.39 kg per meter of planting of 'DrisRaspNine' to 6.62 kg per meter of planting of 'DrisRaspNine' of fruit per season when grown in Oxnard, Calif.

Pest and disease resistance:

*Tetranychus urticae*.—Moderately susceptible.

*Powdery mildew*.—Moderately resistant.

COMPARISON WITH PARENTAL AND COMMERCIAL VARIETIES

'DrisRaspNine' differs from the proprietary female parent 'RB629.4' (unpatented) in that 'DrisRaspNine' has a higher percentage of marketable fruit and the fruit has better flavor than the fruit of 'RB629.4'. Additionally, plants of 'DrisRaspNine' have a more vigorous growth habit and better emergence of canes after planting than 'RB629.4'.

'DrisRaspNine' differs from the proprietary male parent 'RB629.5' (unpatented) in that 'DrisRaspNine' has brighter colored, firmer fruit than 'RB629.5'.

'DrisRaspNine' differs from the commercial variety 'Driscoll Maravilla' (U.S. Plant Pat. No. 14,804), in that 'DrisRaspNine' has medium sized, soft fruit having an easy adherence to the plug, whereas 'Driscoll Maravilla' has large sized, firm fruit having a medium adherence to the plug. Additionally, 'DrisRaspNine' usually has three lateral leaflets with a free arrangement, whereas 'Driscoll Maravilla' usually has five lateral leaflets with an overlapping arrangement.

'DrisRaspNine' differs from the commercial variety 'DrisRaspSeven' (U.S. Plant Pat. No. 25,045) in that 'DrisRaspNine' has medium sized, soft fruit with an ovate shape, whereas 'DrisRaspSeven' has large sized, medium firm fruit with a long conical shape. Additionally, 'DrisRaspNine' usually has three lateral leaflets and terminal leaflets that are convex in cross section, whereas 'DrisRaspSeven' usually has five lateral leaflets and terminal leaflets that are flat in cross section.

We claim:

1. A new and distinct variety of raspberry plant named 'DrisRaspNine', substantially as illustrated and described herein.

* * * * *